United States Patent [19]

Koike

[11] Patent Number: 5,026,282
[45] Date of Patent: Jun. 25, 1991

[54] PHYSIOLOGICAL STEREO ARTICULATOR

[76] Inventor: Isao Koike, 7-chome, Minami, Fukuoka 815, Japan

[21] Appl. No.: 445,865

[22] PCT Filed: Mar. 30, 1989

[86] PCT No.: PCT/JP89/00335
§ 371 Date: Nov. 28, 1989
§ 102(e) Date: Nov. 28, 1989

[87] PCT Pub. No.: WO89/09033
PCT Pub. Date: Oct. 5, 1989

[30] Foreign Application Priority Data

Apr. 1, 1988 [JP] Japan .................................. 63-81638

[51] Int. Cl.$^5$ .............................................. A61C 11/00
[52] U.S. Cl. .......................................... 433/62; 433/58; 433/61
[58] Field of Search ...................... 433/57, 58, 59, 61, 433/62, 63, 64, 65

[56] References Cited

U.S. PATENT DOCUMENTS

| 1,022,055 | 4/1912 | Weiss | 433/64 |
| 1,848,267 | 3/1932 | Perkins | 433/65 |
| 2,269,061 | 1/1942 | Nerbas | 433/65 |
| 2,608,761 | 9/1952 | Scott | 433/58 |
| 3,815,242 | 6/1974 | Martfay et al. | 433/63 |
| 3,908,271 | 9/1975 | Derda et al. | 433/65 |
| 4,189,837 | 2/1980 | Stele | 433/57 |

FOREIGN PATENT DOCUMENTS 2447710 10/1980 France .................................. 433/58

Primary Examiner—John J. Wilson
Attorney, Agent, or Firm—Jordan and Hamburg

[57] ABSTRACT

This invention relates to a physiological stereo articulator comprises a maxillary mechanism and a mandibular mechanism, and the lower frame member in the mandibular mechanism can turn about a center which is shifting while opening and closing as the human mandible does, and at the same time with the shifting of the center of turning, the vertical swinging of the lower frame member is caused. This construction permits simulation of the movement of the lower frame member to practical movement of the human mandible.

11 Claims, 8 Drawing Sheets

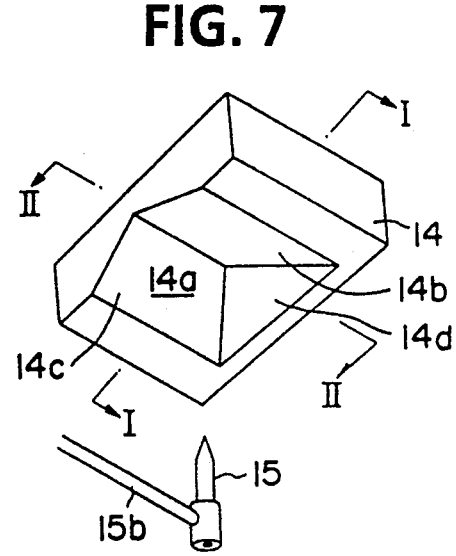
FIG. 7
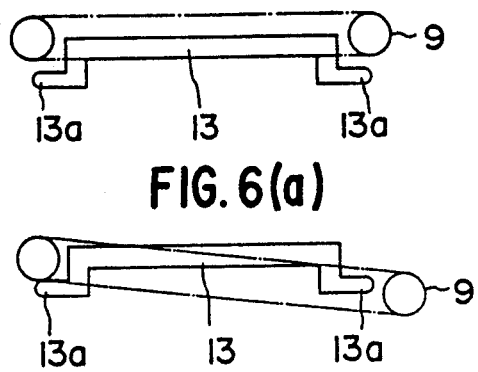
FIG. 6(a)
FIG. 6(b)
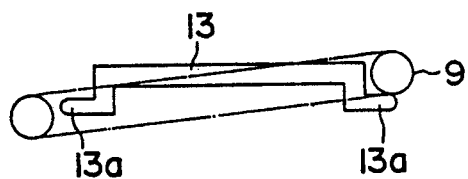
FIG. 6(c)
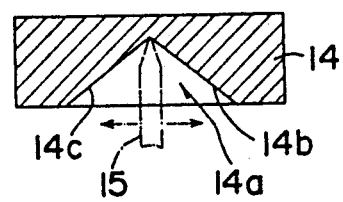
FIG. 8(a)
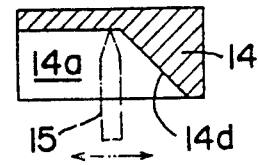
FIG. 8(b)

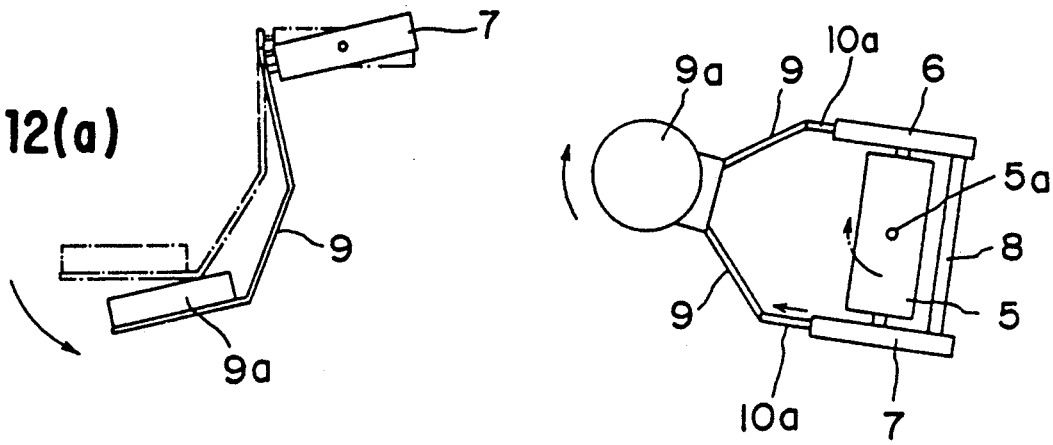
FIG. 12(a)
FIG. 12(b)
FIG. 13
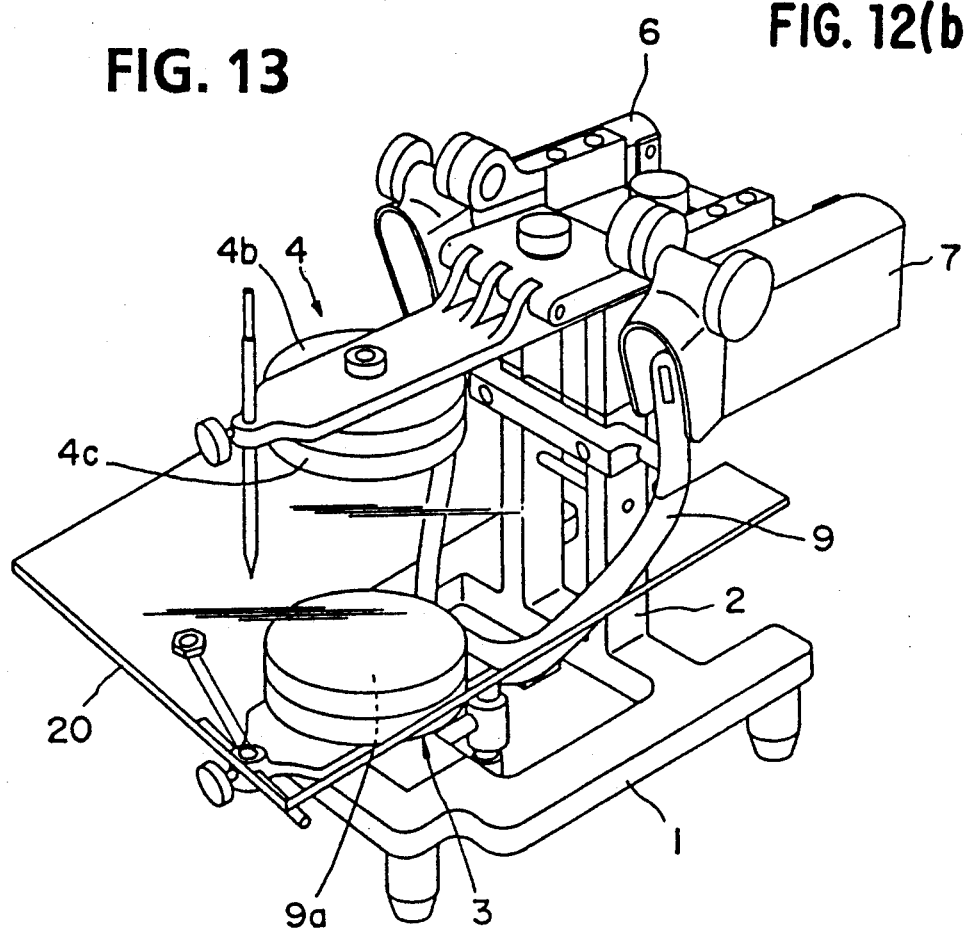

FIG. 14
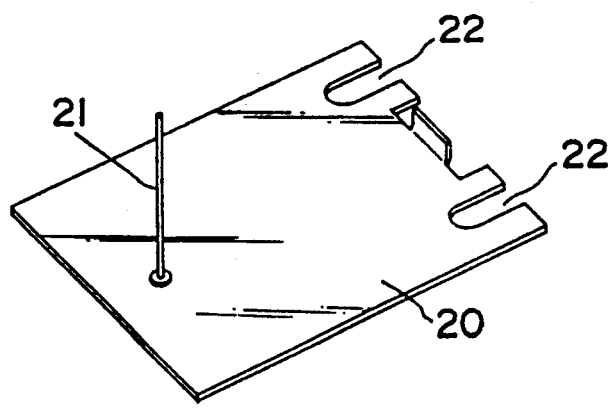
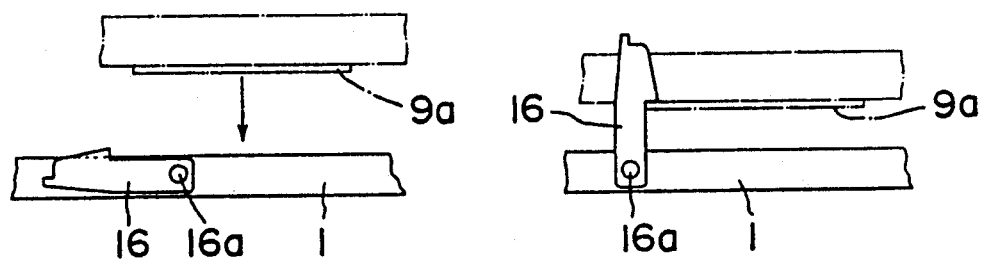
FIG. 15(a)   FIG. 15(b)

PHYSIOLOGICAL STEREO ARTICULATOR

FIELD OF ART

The present invention relates to a physiological stereo articulator used for manufacturing prostheses or the like, with plaster casts attached to the articulator.

BACKGROUND OF THE INVENTION

The most important function of teeth is to chew. The object of treating decayed teeth is to restore as natural occlusion as possible. There are stereo articulators of a type in which the simulation of dental occlusion is possible and in virtue of this, removable partial dentures and full dentures, bridges and crowns, of which the functions are matched to that of the human tooth can be manufactured. A variety of stereo articulators of this type have been developed, for example, as described in "Dictionary of Dental Occlusion" (issued on Mar. 20, 1979 by Shorin Co., Ltd.).

Of these are extensively known the so-called arcon full-adjustable articulator comprising an upper frame member with a condylar guide part, which is a path along which the capitulum mandible travels as the mandible moves, and a lower frame member with a condyle part, and also a simulator articulator where the structural parts can be adjusted to average values of anatomy.

The structure in human permits the lower jaw to swing around the movable fulcrum on the maxilla while the arcon full-adjustable articulator has the construction that the upper frame member moves around the condyle part on the lower frame.

All the conventional articulators mentioned above are of the type in which, unlike the structure in human, the upper frame moves. Viewing from the structure in human, the practical measurement data of inclination of condyle path, and sideward, forward and opening movements has revealed that they were very unnatural, and besides dynamical study on occlusion buffer has demonstrated that partial pressure on teeth was distributed. For these reasons, the structure remained as a basic problem. Also another type of articulator has been developed intending to solve this problem which comes from the construction that the movable frame members were disposed reversely to the structure in the human and therefore in which a condyle is provided on the upper frame member to permit the lower frame member to be movable.

Occlusal movement in the human is very complicated, and hence to realize a physiological stereo articulator of the type in which the lower frame member is movable is not simple to such an extent that to the contrary of the arcon full-adjustable articulator, a condyle is fixed to the upper frame member instead of the upper frame but it is required to be a structure permitting the lower frame member to completely simulate the real condyle path.

The principal object of the present invention is to provide a physiological stereo articulator comprising a lower frame member movable conforming with the most fidelity the condyle path in the human.

DISCLOSURE OF THE INVENTION

The present invention is an articulator which permits accurate simulation compared with the prior art and which has such construction that the movement pattern of the lower frame member consisting of the movement of the anterior teeth free-end to predict a locus of circular arc as the mouth opens and the forward and downward movement of the temporomandiblar caput, as known so far, can be corrected by addition of the shift of the fulcrum of movement.

BRIEF DESCRIPTION OF DRAWINGS

FIGS. 6a, 6b and 6c are plan views schematically showing the positional relationships between the lower frame member and a rest bar;
FIG. 7 is a bottom perspective view;
FIGS. 8a and 8b are sectional views taken along lines I—I and II—II, respectively;
FIGS. 12a and 12b are similar illustration with the lower frame member left-turned when viewed from the front;
FIG. 13 is a perspective view when a fixing plate is set;
FIG. 14 is a perspective view of the fixing plate;
FIGS. 15a and 15b illustrate locking of mounting plate.

DESCRIPTION OF THE PREFERRED EMBODIMENT

Figure 16:
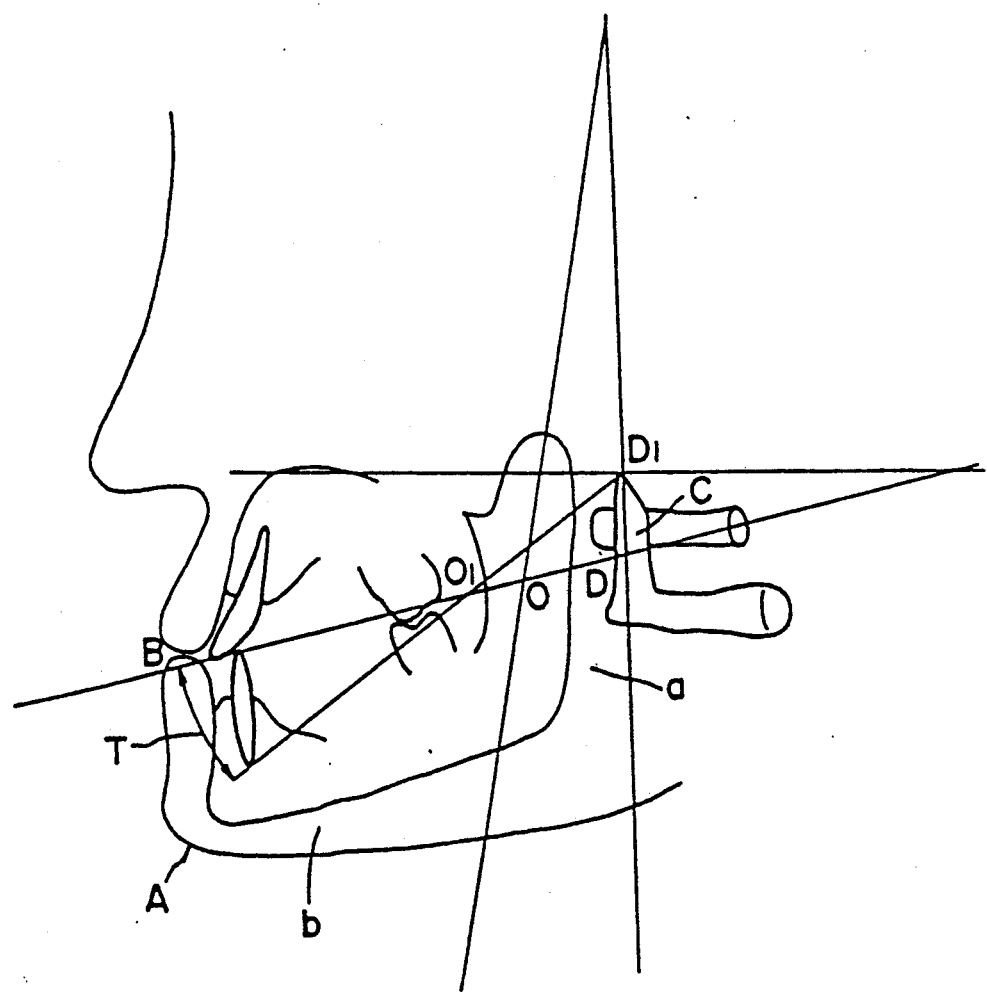
FIG. 16 shows the basic pattern of the movement of the human mouth.

FIG. 16 is a diagram illustrative of the opening and closing of the human mouth, particularly the locus of movement of the upper end B of the lower central incisors.

Referring to FIG. 16, as the mandible A composed of the vertical ramus "a" and bow body "b" moves to open, the upper end "B" of the lower central incisors predicts a locus "T" along the arc in the second quadrant of a circle of as the center, point "O" on the vertical ramus "a" and as a radius the distance between the center "O" and the upper end "B" of the lower central incisors which is the front end of the occlusal-plane straight line.

The locus "T" is not completely circular. The turning center "O" moves to point "$O_1$" as the mandible opens at a certain inclination on the vertical ramus "a" of the mandible A. Then the intersection "D" of the occlusal-plane straight line BO and the second cervical-tooth process "C" moves on the process "C" to the point "$D_1$"

Thus the present invention relates to particularly a mandibular mechanism permitting the realization of substantially-practical occlusion with good efficiency in the form of the lotus along which the upper end of the central incisors moves as shown in FIG. 16, which is represented by taking the movement on the extension of the turning radius as the movement of the turning center.

Figure 1:
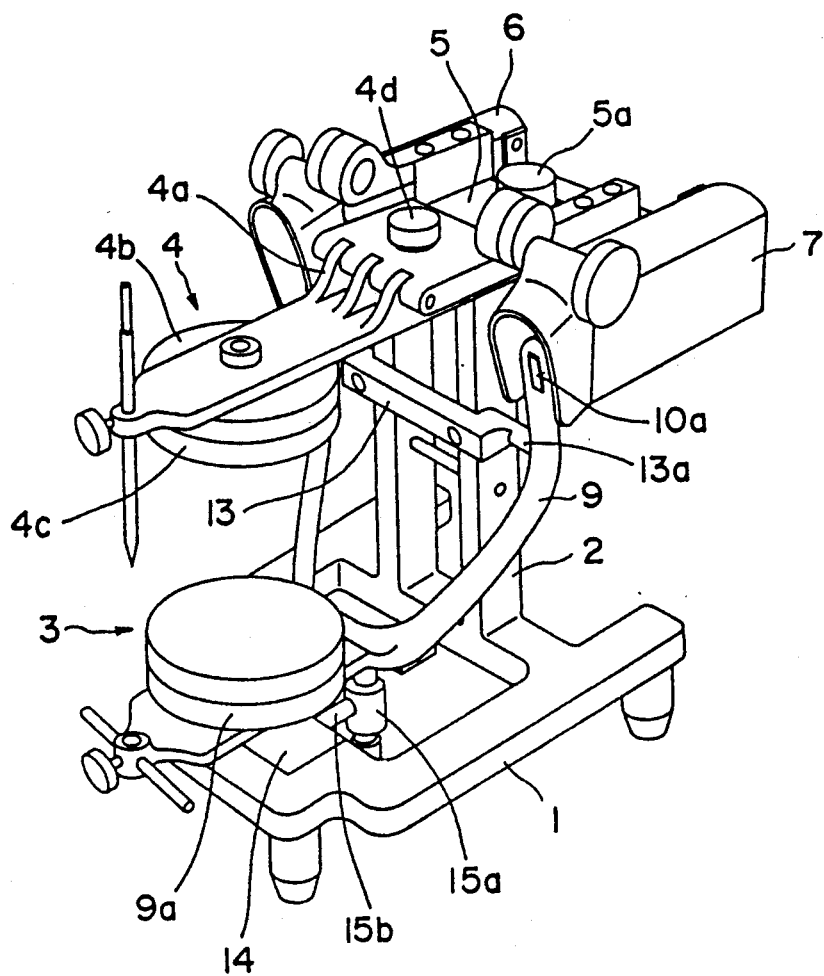
FIG. 1 is a perspective view of an articulator according to the present invention.
Figure 2:
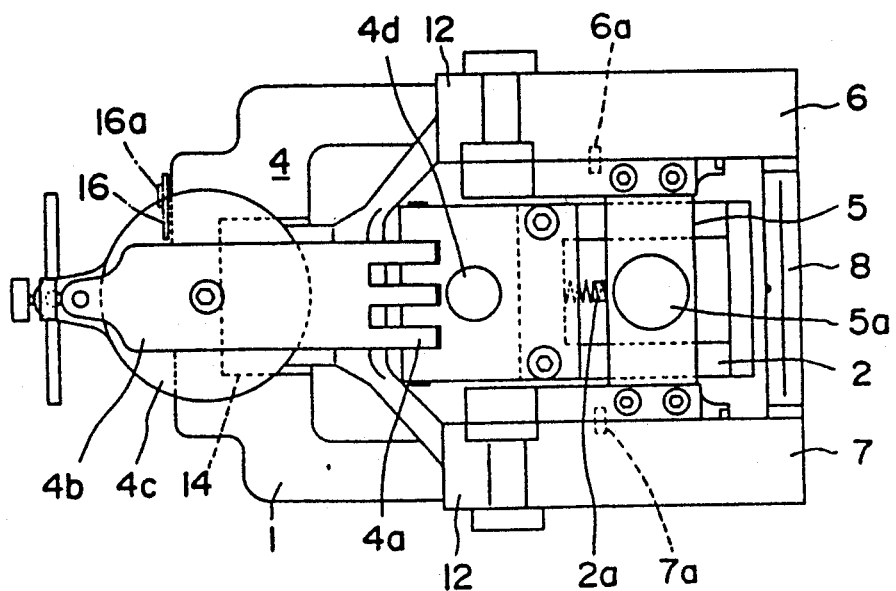
FIG. 2 is a plan view of the same.
Figure 3:
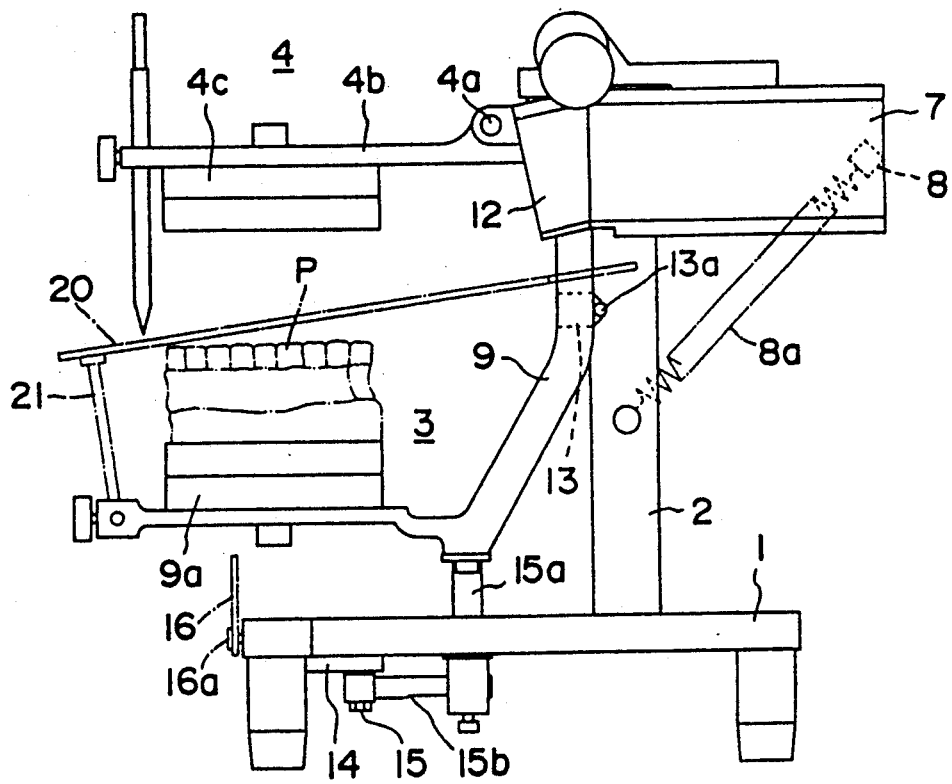
FIG. 3 is a side view of the same.

In the following, the features of the present invention will be described by way of examples with reference to the drawing:

FIG. 1 is a perspective view of an articulator embodying the present invention and FIGS. 2 and 3 are plan and side views of the same, respectively.

In these Figures, the articulator is a occluding frame including a frame base 1, a post 2, and mandibular and maxillary mechanisms 3 and 4 connected to the post 2 at the upper end of thereof.

The maxillary mechanism 4 comprises an upper frame member 4b in the front of and mounted pivotally on a hinge 4a at the upper end of the post 2 to be swingable vertically. The upper frame is provided on the undersurface of the free end with a mounting plate 4c to which a plaster cast should be attached, and at the other end an operational screw 4d is screwed down through the hinge 4a into the maxillary frame member 4b. By loosening the screw 4d and removing it, and the maxillary frame 4b can be opened up.

On the other hand, the mandibular mechanism 3 is connected with a swingable base 5 which is mounted on a pivot shaft 5a at the upper end of the post 2. A coil 2a provided between the swingable base 5 and the post 2. The swingable base 5 includes a pair of operating blocks 6, 7, each on the left and right side, respectively, and is mounted pivotally on pivot shafts 6a, 7a, respectively, to be swingable vertically. The operating blocks 6, 7 are integrated with each other by means of a connecting rod 8. A spring 8a is provided between the middle of the connecting rod 8 and the post. The spring 8a, which is a tension coil spring, urges the rear ends of the operating blocks 6, 7 clockwise around the pivot shafts 6a, 7a as shown in FIG. 3.

The operating blocks 6, 7 are connected with a pair of branches of the lower frame member 9. The lower frame member 9 comprises vertically-extending portions and forward and gradually bowing portions, and at the front end a mounting plate 9a is integrated with these, as shown in FIGS. 1 and 3.

Figure 4:
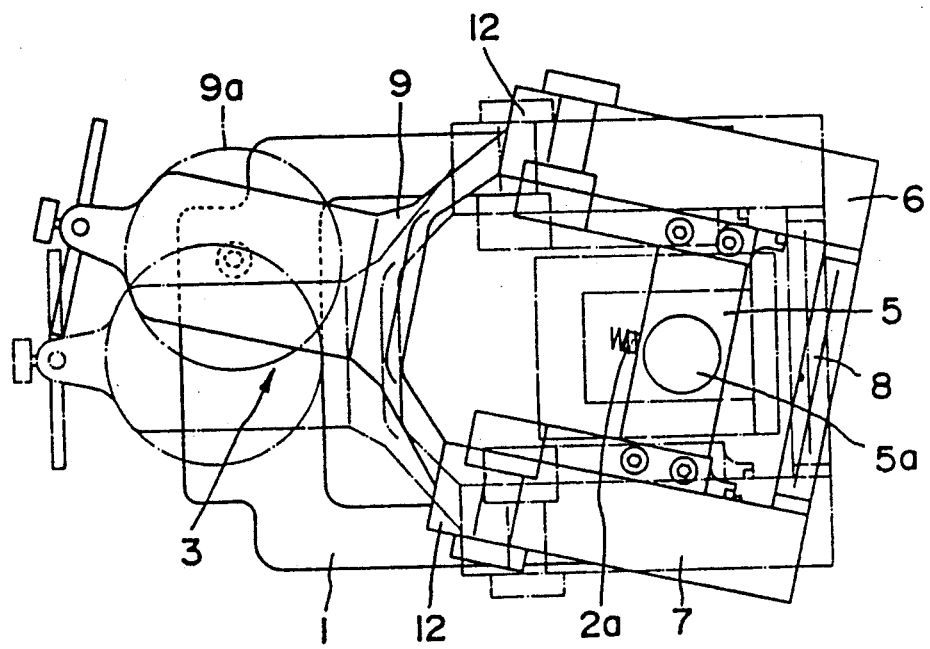
FIG. 4 is a plan view of the same illustrating the swinging of the mandibular mechanisms.

FIG. 4 is a plan view of the articulator with the swingable base 5 and the mandibular mechanism 3 together turned to the left when viewed from the front. As shown, the swingable base 5 is in a position clockwise turned around the pivot shaft 5a and also the mounting plate 9a is in the left-shifted and retreated position. In the case of a practical movement, as described later, the mounting plate 9a moves a little back, and bows forwards. The operation of the mandibular mechanism 3 can be accomplished by means of the operating blocks 6, 7 and other mechanisms.

Figure 5A:
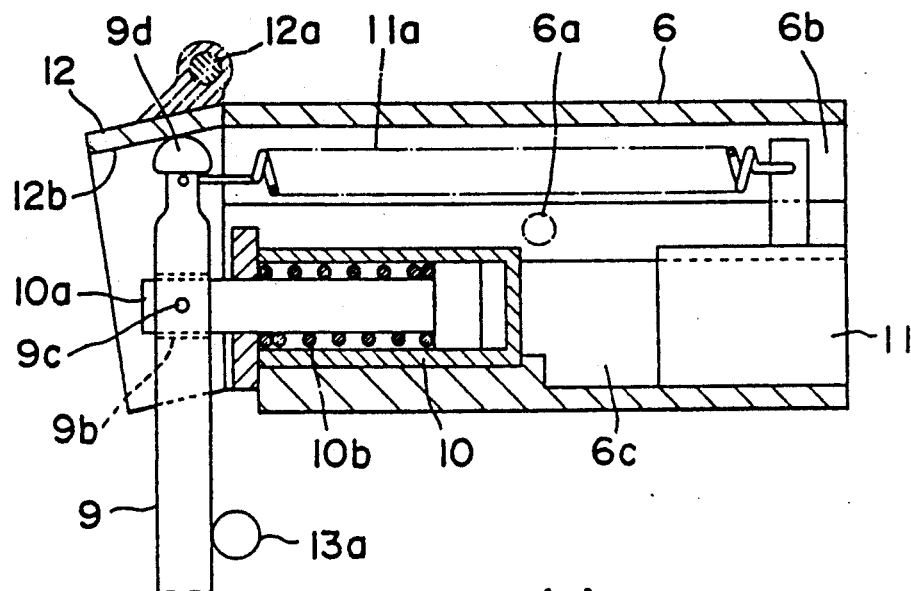
FIG. 5a is a longitudinal sectional view of an operating block.

FIG. 5 is a longitudinal sectional view of the operating block 6. The operating block 6 is provided with bores 6b, 6c of which axes are longitudinally extending in parallel over the overall length of it. In the front end portion of the lower bore 6c, there is provided a cylinder 10 in which an actuator 10a is fitted. The actuator 10a projects forward from the cylinder 10, and this projecting portion passes through a connection bore 9b in the lower frame member 9 and is pivotally connected by means of a pin 9c to the lower frame member. There is provided in the cylinder 10 a compression coil spring 10b which always urges the actuator 10a to the right in FIG. 5 and in turn the lower frame member 9 toward the operating block 6. In the rear portion of the bore 6c, a slider block 11 is fitted to be axially slidable. There is provided in the bore 6b a tension coil spring 11a through which the slider block 11 and the upper end of the lower frame member 9 are interconnected.

At the front end of the operating block 6, a cover 12 of which undersurface 12b abuts against a hemispherical head 9d at the upper end of the lower frame member 9 is, as shown in FIG. 5, oblique front lower and pivotally mounted on the pivot shaft 12a to swing vertically so that the lower frame member 9 is forced to move up and down. Besides the right-hand operating block 7 is constructed in entirely the same way, of which detailed description therefore is omitted.

The lower frame member 9 to be operated by the operating blocks 6, 7 rests on a bar 13 serving as a rest for the swinging lower frame member. The fulcrum bar 13 is bridged between the vertical straight portions of the lower frame member 9 as shown in FIGS. 1 and 2. FIGS. 6a, 6b and 6c are plan views schematically showing positional relationship of the lower frame member 9 to the rest bar 13 with behind-bowed ends (called "fulcrum portions" hereinafter) 13a each having a substantially-circular section and serving as a fulcrum.

FIG. 6a shows when the mandibular mechanism 3 is in the center position, and a slight gap is provided between the hind peripheries of the branches of the lower frame member 9 and the fulcrum portions 13a. Alternatively it may be designated so that there is no gap but the lower frame member 9 touches lightly on the fulcrum part 13a. FIG. 6b shows when the actuator 10a of the operating block 7 is protruded and in the left-turned position when the lower frame member 9 is viewed from the front, and the FIG. 6c does likewise but when the actuator 10a is in the reverse of right-turned position, respectively.

On the frame base 1 is mounted a guide block 14 for forcing the lower frame member 9 down. The guide block 14, as shown in FIG. 3, is disposed in the front portion of the frame base 1 and constructed to receive a guide pin 15 connected to the lower end of the lower frame member 9. The guide pin 15 is held by a horizontal extending arm 15b connected through a vertically-extending rod 15a to the lower end of the lower frame member 9. In FIG. 3, the guide pin 15 is found in a vertical position.

FIG. 7 is a perspective view of the guide block 14 when viewed from the bottom. FIGS. 8a and 8b are cross-sectional views taken along lines I—I and II—II of FIG. 7.

As shown, the bottom of the guide block 14 is provided with a prism-shaped depression 14a extending widthwise, of which the right, left and fore oblique walls 14b, 14c, 14d abut against the guide pin 15 as shown in FIG. 8. When moved left- or rightwards from the position shown in FIG. 8a, the guide pin 15 is forced down because of the abutment against the ablique wall 14b or 14c, and in turn the lower frame member 9 moves left- or rightwards while inclining front down. Similarly when moved forwards from the position shown in FIG. 8b, the guide pin moves forwards along the oblique wall of the guide block 14, and thus the lower frame member moves forwards while inclining front down.

The lower frame member 9 with a mounting plate 9a makes approximate movement to human mandibular motion while carrying a plaster cast attached to the mounting plate 9a. This will be described with reference to FIGS. 9 through 12.

Figure 9A:
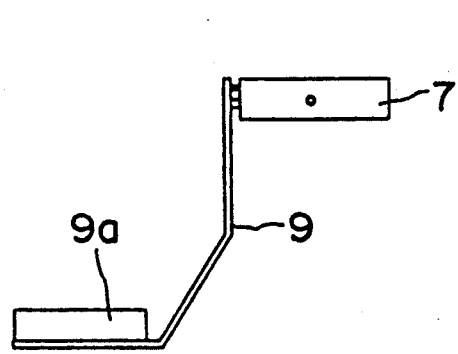
FIGS. 9a and 9b illustrate the posture of the lower frame member when closed.
Figure 9B:
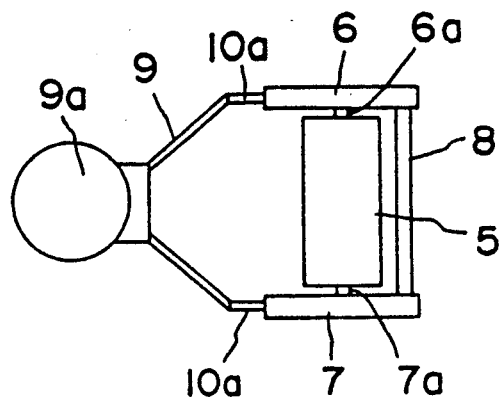

FIGS. 9a and 9b illustrate schematically the lower frame member 9 in the usual closed position. As shown, the mounting plate 9a is positioned approximately horizontally, and the swingable base 5 is in the center position.

Figure 5B:
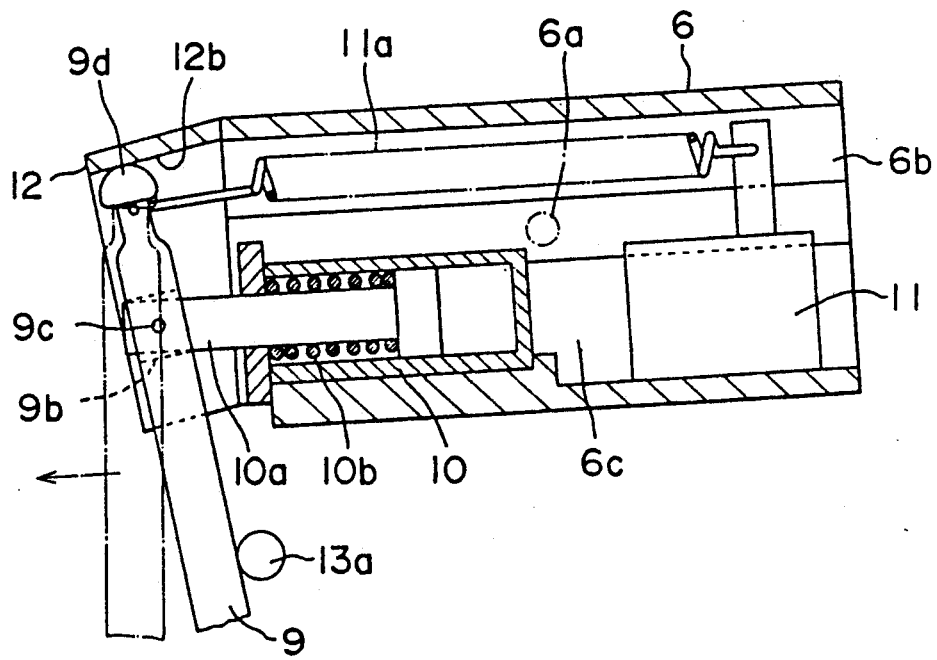
FIG. 5b is a similar longitudinal sectional view illustrating the pivotal movement of the lower frame member.
Figure 10A:
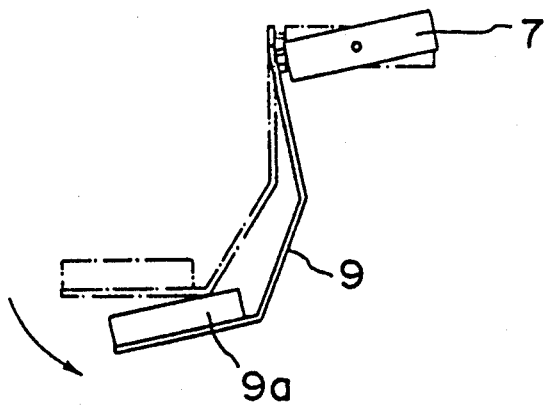
FIGS. 10a and 10b are similar illustration when the lower frame member is in the forced down position.
Figure 10B:
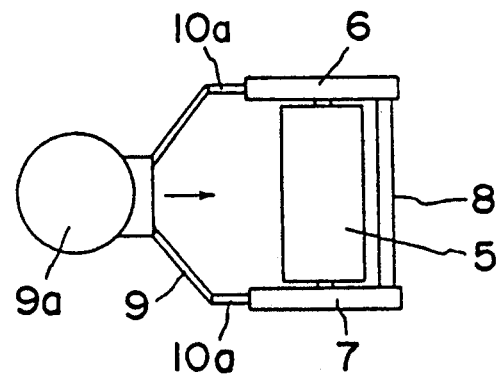

In FIGS. 10a and 10b, the lower frame member 9 in the froced-down position is illustrated with the solid line and that in the closed position of FIG. 9 with the dash-and-dot line. As illustrated in FIG. 10a, upon causing the mounting plate 9a to lower, the lower frame member 9 is caused to turn counterclockwise and at the same time also the operating blocks 6, 7 turn about the pivot shafts 6a, 7a to be in a front-down inclined position. This operation will be described more fully referring to FIG. 5 in the following: If the mounting plate 9a is forced down, the lower frame member 9 turns in such a way that the lower end portion of it moves back, that is, from the closed position shown in FIG. 5a to the position of FIG. 5b. In this movement, the center of turning of the lower frame member 9 should be point contacting with the fulcrum part 13a because the lower frame member 9 abuts against the fulcrum part 13a of the rest bar 13 while turning. Thereafter in the operating blocks 6, 7 as shown in FIG. 5b, the slider block 11 and in turn the actuator 10a in the cylinder 10 move forth. This results in the abutment of the hemispherical head 9d of the lower frame member 9 against the oblique undersurface of the cover 12 to cause the blocks 6, 7 to turn around the pivot shafts 6a, 7a to be in the front-down inclined position.

From the above-mentioned, forcing the front extremity of the lower frame member down causes the lower frame member to turn counterclockwise around the shifting abutments on the fulcrum portions 13a as centers of the movement. In other words, with this turning, the lower frame member 9 causes the operating blocks 6, 7 to incline front down, and thus the abutment between the lower frame member 9 and the fulcrum part 13a shifts to higher level. In summary, while the lower frame member 9 is moving downwards under contact with the fulcrum part 13, the center of the swinging is shifting with the passage of time. In this way, the mounting plate 9a at the front end of the lower frame member 9 turns downwards with distance between it and the fulcrum part 13a when closed, as the initial radius of turning, and thereafter while predicting the locus of turning with the radius of it getting gradually smaller.

The movement of the lower frame member 9 as described above permits the movement of the mounting plate 9a similar to the opening and closing of the human mandible.

Figure 11A:
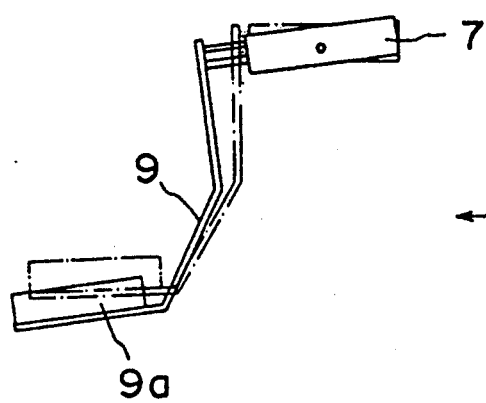
FIGS. 11a and 11b are similar illustration when the lower frame member is in the forward-drawn-out position.
Figure 11B:
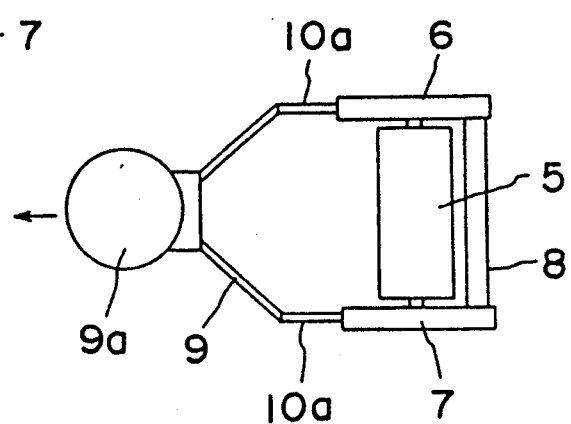

FIGS. 11a and 11b illustrate an example of pulling forwards the mounting plate 9a, which causes forward or rightward (when viewed in FIG. 8b) movement of the guide pin 15 on the lower frame member 9 to reach the undersurface of the downward-inclined wall 14d and then advance while profiling it. This results in forward movement of the lower frame member 9 with the mounting plate 9a inclined front lower, and in turn the actuators 10a of the operating blocks 6, 7 are drawn out. Then the hemispherical head 9d of the lower frame member is forced against the undersurface 12b of the cover 12 with the same consequence as described in FIG. 10, that the operating blocks 6, 7 is caused to incline front lower.

As described above, also the forward movement of the mounting plate 9a can be accomplished in just a similar way to the movement of the human mandible in virtue of the guide by means of the guide block 14 and the shifting of the center of turning resulting from the inclination of the operating blocks 6, 7.

FIGS. 12a and 12b illustrate an example when the mounting plate 9a is in the left-turned position when viewed from the front.

Upon forcing the mounting plate 9a leftwards, the swingable base 5 turns round the pivot shaft 5a as shown in FIG. 4. Then the guide pin 15 fixed to the lower frame member 9 moves rightwards in FIG. 8a, and is forced down against the oblique wall 14b. As the result, at the same time with the leftward turning, the lower frame member 9 moves down. The synthesis of the turning and the downward movement causes the mounting plate 9a to move leftwards and then down, and at the same time to a position inclined front lower as shown in FIG. 12a. As the result of the turning of the lower frame member 9, also the lower frame member 9 shifts to the position inclined with respect to the bar 13 as shown in FIG. 6b.

Also in such leftwards movement, as in the case of FIG. 10, the change in position of the center of turning of the lower frame member 9 permits the movement of the mounting plate 9a just similar to the movement of the human mandible.

By forcing the mounting plate 9a toward the left in FIG. 12, the lower frame member 9 can turn clockwise with drawing of the actuator 10a out of the operating block 7 on the right side when viewed from the front. In other words, the swingable base 5 can turn with the withdrawal of the actuator 10a into the operating block 7 on the left side and substantially without movement of the actuator 10a in the operating block 7 on the right side. After reaching the maximum degree of turning of the turning vase 5, further forcing the mounting plate 9a toward the left causes additional left shift in position of the lower frame member 9 in excess of the maximum degree of turning with drawing of the actuator 10a from the operating block 7. This is illustrated in FIG. 12b in which the lower frame member 9 moves left in excess of the turning limit of the swingable base 5.

There may be provided a fixing plate 20 associated with the mounting plate 9a, which is used for fixing a plaster cast to the mounting plate 9a when the former is placed on the latter. As shown in FIG. 13, the fixing plate 20 is secured to the bridge between the mounting plate 9a and the branches of the lower frame member. The fixing plate 20 is made of a material such as a transparent plastic plate, and as shown in FIG. 14, is provided with studs 21 on one surface, and notches 22 at one edge in which the branches of the lower frame member 9 fit in. The fixing plate 20 is set at a suitable level of height, as shown in FIG. 13, to keep in place the upper surface of a plaster cast "P" as shown with the dash-and-dot in FIG. 3, and its transparency allows observation through it. At the front the frame base 1 is mounted on a lock plate 16 for preventing the mounting plate 9a from further lowering, as shown in FIGS. 2 and 3. It is allowed to turn by means of a pin 16a. FIGS. 15a and 15b are front views including the lock plate 16 which is caused to shift to the standing position shown in FIG. 15b when the mounting plate 9a is lowered whereby the latter can be supported by the lock plate 16.

Now for construction it is assumed that the distance between the upper ends of the lower frame member 9 and points contacting with the fulcrum parts 13a of the rest bar 13 is equal to the distance between the hard palate and occlusal plane in FIG. 16. This permits the shift of the contact points of the fulcrum parts 13a with the lower frame member 9, which occurs from the turning of the lower frame member 9 to correspond to the shift from the center of swinging "O" to "$O_1$". Thus the movement of the lower frame member 9 can be very similar to the movement of the mandible in the mouth.

The lower frame member 9 can be moved back and forth by means of the operating blocks 6, 7 and thus the position of the mounting plate 9a can be set suitably every patient. The characteristic of plaster cast for the individual can be represented with accuracy.

The physiological articulator according to the invention has advantages mentioned in the following:

a. The appropriate representation of the behavior of the patient's teeth permits improved accuracy of therapeutic effect:

b. The specification of the articulator itself is basically similar to the conventional articulators. This enable them to be used without substantial change nor making a healer feel unacceptable; and c. Simple in structure, light in weight, and therefore can be used in any mode of use.

INDUSTRIAL FEASIBILITY

The present invention can be used in the entire field utilizing articulators for simulating practical occlusion condition in human with use of plaster casts in dental treatment.

I claim:

1. An articulator comprising:
    a frame having a frame base and a frame upright;
    a maxillary mechanism comprising an upper frame member pivotably mounted on said frame upright for pivotable movement about a horizontal axis;
    a mandibular mechanism comprising a base part pivotably mounted on said frame upright for pivotal movement about a vertical axis, said mandibular mechanism comprising a lower frame member and support means supporting said lower frame member;
    said support means comprising operating blocks pivotably mounted on said base part, said operating blocks having extendable and retractable activators, pivot means pivotably mounting said lower frame member on said activators, said operating blocks having an inclined surface engageable by said lower frame member as said activators extend and retract such that said engagement effects pivoting of said operating blocks to thereby effect raising and lowering of said lower frame member.

2. An acticulator according too claim 1 further comprising fulcrum engagement means mounted on said frame upright and engageable by said lower frame member to define a fulcrum axis for said lower frame member, the position of said fulcrum axis on said lower frame member changing as said lower frame member is raised and lowered by said extendable and retractable activators.

3. An articulator according to claim 2, wherein said lower frame member has two branches each having an upper generally vertical end section, said pivot means pivotably connecting said end sections to said activators, said lower frame member having a horizontal front section from which said two branches extend, said vertical end sections each having a front side and a rear side, said activators being disposed on the rear side of said vertical end sections, said fulcrum engagement means generally underlying said activators and being engageable with said rear side of said vertical end sections.

4. An articulator according to claim 3, wherein said fulcrum engagement means comprises two fulcrum parts with one fulcrum part being engageable with the rear side of the vertical end section of one of said branches and the other fulcrum part being engageable with the rear side of the vertical end section of the other of said branches.

5. An articulator according to claim 1, wherein said lower frame member has hemispherical surfaces engageable with said inclined surface of said operating blocks.

6. An articulator according to claim 1, wherein said operating blocks have biasing means biasing said activators toward a retracted position.

7. An articulator according to claim 1, wherein there are two of said operating blocks, further comprising connecting means connecting said two operating blocks together, and biasing means between said connecting means and said frame upright biasing said two operating blocks in one pivotal direction.

8. An articulator according to claim 1, wherein said frame base has a guide block underlying said lower frame member, said guide block having a depression formed by oblique walls which are inclined relative to horizontal, said lower frame member having a guide pin operable in said depressions and operable to engage said oblique walls for moving said lower frame member.

9. An articulator according to claim 8, wherein two of said oblique walls intersect one another along a line of intersection in a V-shaped configuration, at least one other of said oblique walls being disposed at an acute angle relative to said line of intersection.

10. An articulator comprising:
    a frame having a frame base and a frame upright;
    a maxillary mechanism comprising an upper frame member pivotably mounted on said frame upright for pivotable movement about a horizontal axis;
    a mandibular mechanism comprising a base part mounted on said frame upright for pivotal movement about a vertical axis, said mandibular mechanism comprising a lower frame member and support means supporting said lower frame member;
    said support means comprising operating blocks pivotably mounted on said base part, said operating blocks having extendable and retractable activators, pivot means pivotably mounting said lower frame member on said activators;
    said frame base having a guide block underlying said lower frame member, said guide block having a depression formed by engageable walls which are inclined relative to horizontal, said lower frame member having a guide pin operable in said depression and operable to engage said engageable walls for moving said lower frame member.

11. An articulator comprising:
    a frame having a base and a frame upright;
    a maxillary mechanism comprising an upper frame member pivotably mounted on said frame upright for pivotable movement about a horizontal axis;
    a mandibular mechanism comprising a base part pivotably mounted on said frame upright for pivotal movement about a vertical axis, said mandibular mechanism comprising a lower frame member and support means supporting said lower frame member;

said support means comprising operating blocks pivotably mounted on said base part, said operating blocks having extendable and retractable activators, pivot means pivotably mounting said lower frame member on said activators, said operating blocks having surface means engageable by said lower frame member as said activators extend and retract such that said engagement effects pivoting of said operating blocks to thereby effect raising and lowering of said lower frame member; and fulcrum engagement means mounted on said frame upright and engageable by said lower frame member to define a fulcrum axis for said lower frame member, the position of said fulcrum axis on said lower frame member changing as said lower frame member is raised and lowered by said extendable and retractable activators.

* * * * *